United States Patent [19]

Rubner et al.

[11] 4,329,556
[45] May 11, 1982

[54] N-AZIDOSULFONYLARYL-MALEINI-MIDES

[75] Inventors: Roland Rubner, Röttenbach; Eberhard Kühn, Hemhofen; Hellmut Ahne, Röttenbach, all of Fed. Rep. of Germany

[73] Assignee: Siemens Aktiengesellschaft, Munich, Fed. Rep. of Germany

[21] Appl. No.: 148,142

[22] Filed: May 9, 1980

[30] Foreign Application Priority Data

May 16, 1979 [DE] Fed. Rep. of Germany ....... 2919823

[51] Int. Cl.$^3$ .............. C07D 207/452; C07D 207/456
[52] U.S. Cl. .................................................. 548/549
[58] Field of Search .............................. 260/326.5 FM

[56] References Cited

U.S. PATENT DOCUMENTS 4,130,564  4/1975  Hang et al. ............... 260/326.5 FM

FOREIGN PATENT DOCUMENTS 2715503  10/1977  Fed. Rep. of Germany ... 260/326.5 FM
2722513  11/1978  Fed. Rep. of Germany ... 260/326.5 FM

*Primary Examiner*—Anton H. Sutto
*Assistant Examiner*—D. B. Springer
*Attorney, Agent, or Firm*—Kenyon & Kenyon

[57] ABSTRACT

The invention relates to new arylsulfonylazides as well as the use of these compounds. The new compounds are characterized by the general formula:

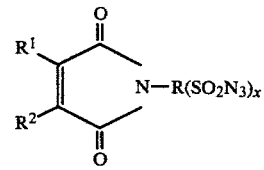

where R=aryl; x=1 or 2; and $R^1$ and $R^2$ are selected from H, $CH_3$ and Cl and may be the same or different, with the provision that $CH_3$ and Cl are not present side by side. The compounds according to the invention are suitable as photoinitiators in the preparation of relief structures by phototechniques from olefinically unsaturated polymers, as well as cross-link enhancing agents in the radical-wise cross linking of thermoplastic polymers.

2 Claims, No Drawings

N-AZIDOSULFONYLARYL-MALEINIMIDES

The invention relates to new arylsulfonylazides as well as to the use of these compounds.

The invention relates in particular to N-Azidosulfonylaryl-maleinimides of the general formula

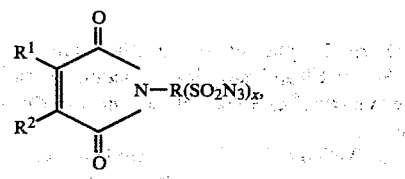

where R=aryl; x=1 or 2; and $R^1$ and $R^2$ have the meaning H, $CH_3$ and Cl and may be the same or different provided that $CH_3$ and Cl are not present side by side. "Aryl" is understood here to mean aromatic hydrocarbon radicals such as phenyl and naphthyl. A preferred compound is N-(4-azidosulfonylphenyl)-maleinimide. Other compounds are, for example, 2-(N-maleinimido)-naphthyl-5-sulfonylazide and 2-(N-maleinimido)-naphthyl-6,8-bissulfonylazide.

The new compounds are prepared, for example, from acetyl-aminobenzenesulfonic acid chlorides via the corresponding aminobenzenesulfonylazides in the following manner:

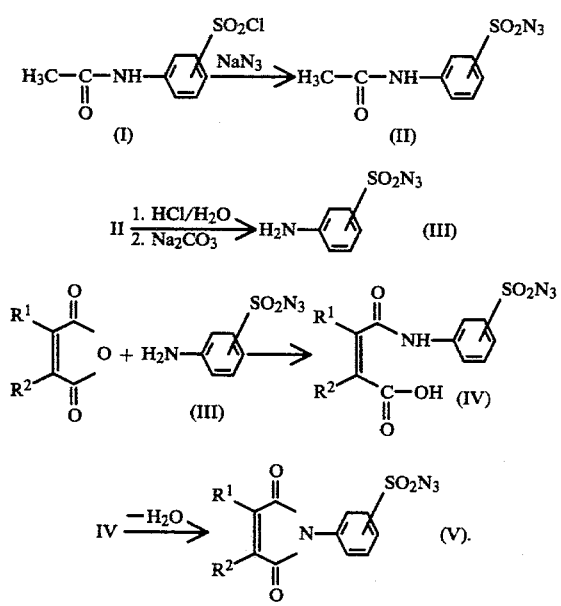

The compounds according to the invention are suitable as photo-initiators in the preparation of relief structures by phototechniques from mixtures which contain olefinically unsaturated polymers and, as photo-initiators, azides. Such a method is described in our commonly-assigned, concurrently-filed U.S. Patent Application Ser. No. 148,129, now U.S. Pat. No. 4,287,294, entitled "Method For the Preparation of Relief Structures By Phototechniques" (VPA 79 P 7515). In addition, the compounds according to the invention can be used to advantage as cross-link-enhancing agents in the radical-wise cross-linking of thermoplastic polymers, for example, in the peroxidic cross-linking of polyolefins, especially ethylene-vinyl acetate copolymers (EVA).

The invention will be explained in further detail with reference to the preparation of intermediate and end products.

1. 4-Acetylaminobenzenesulfonylazide 233.5 g 4-acetylaminobenzenesulfonic acid chloride (approximately 1 mol) are added in cold condition (at 2° to 3° C.) and while being stirred into a solution of 70 g sodium azide (approximately 1 mol) in 800 g water. Subsequently, stirring is continued for 18 hours at room temperature and then the temperature is held at 40° C. for one hour; finally, aspiration is applied and washing with excess water follows. A brown substance is obtained.

2. 4-Aminobenzensulfonylazide Hydrochloride

The 4-acetylaminobenzenesulfonylazide obtained according to (1) is stirred with 400 g 32-% aqueous hydrochloric acid and the mixture is brought to a temperature of 95° C. within 20 minutes. The substance goes into solution completely. Upon cooling, the hydrochloride of the 4-aminobenzenesulfonylazide crystallizes out from the hot hydrochloric solution and is filtered off.

3. 4-Aminobenzenesulfonylazide

From the hydrochloride obtained in accordance with (2), the free base is obtained in the usual manner with aqueous soda solution (approximately 100 g $Na_2CO_3$ in 500 ml water) as a quickly solidifying oil. The yield is about 130 to 150 g (approximately 60 to 80% of theoretical). The product is washed with water and dried in a drying cabinet over $P_2O_5$. The melting point of the product is 35° to 36° C.

4. N-(4-Azidosulfonylphenyl)-maleic acid monoamide 100 g maleic acid anhydride are dissolved in 1 liter dichloromethane and to this solution are added dropwise 198 g of the 4-aminobenzenesulfonylazide (approximately 1 mol) prepared according to (3), dissolved in 400 ml dichloromethane. The reaction mixture is left standing for 2 hours at room temperature. The solution is then concentrated in a rotary evaporator to about 200 ml. The light brown product obtained is cooled, filtered, washed with a small amount of dichloromethane and finally dried.

5. N-(4-Azidosulfonylphenyl)-maleinimide 280 g of the maleic acid monoamide prepared in (4) are suspended in 1 liter dichloromethane and to this suspension is added at 0° C. a mixture of 153 g 1-hydroxybenzotriazol $H_2O$ (1 mol) and 230 g N,N'-dicyclohexylcarbodiimide (approximately 1.1 mol). After 12 to 15 hours the precipitated urea is filtered off and the dichloromethane is evaporated. By pulverizing with petroleum ether, the excess N,N'-dicyclohexylcarbodiimide is removed. The product obtained in this manner is purified by column chromatography on silica gel with acetic ester or in a mixture of acetic ester and dichloromethane as a tracking agent.

The N-(4-azidosulfonylphenyl)-maleinimide is obtained in the form of faintly yellowish needles which are soluble in acetone, chloroform, dimethyl acetamide and other common solvents. Its melting point is 120° C. (while being decomposed).

Elementary analysis: calculated C 43.16%; H 2.71%; N 20.14%. found C 42.82%; H 2.16%; N 19.80%.

The IR spectrum shows the following characteristic bands:

| | |
|---|---|
| —N₃ | :2130 cm⁻¹ or 4.69 μm; |
| —CO—N⟨ | :1775 cm⁻¹ or 5.63 μm and 1730 cm⁻¹ or 5.82 μm; |
| ⟩C=C⟨ (aromatic) | :1595 cm⁻¹ or 6.28 μm and 1493 cm⁻¹ or 6.68 μm. |
What is claimed is:
1. N-azidosulfonylaryl-maleinimides of the formula
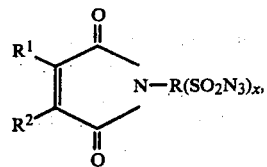
where R=phenyl or naphthyl; and $R^1$ and $R^2$ are H, CH₃ or Cl and may be the same or different, with the provision that $R^1$ and $R^2$ are not, at the same time, CH₃ and Cl.
2. N-(4-azidosulfonylphenyl)-maleinimide.
* * * * *